United States Patent [19]

Sisson

[11] B 3,989,867
[45] Nov. 2, 1976

[54] ABSORPTIVE DEVICES HAVING POROUS BACKSHEET

[75] Inventor: James Bryant Sisson, Hamilton, Ohio

[73] Assignee: The Procter & Gamble Company, Cincinnati, Ohio

[22] Filed: Feb. 16, 1973

[21] Appl. No.: 333,110

[44] Published under the second Trial Voluntary Protest Program on March 16, 1976 as document No. B 333,110.

[52] U.S. Cl. .................................. 428/132; 5/91; 5/354; 128/156; 128/284; 128/296; 428/136; 428/138; 428/155; 428/179; 428/183; 428/188

[51] Int. Cl.² ................ A61F 13/18; A61F 13/20; A61L 15/03; B32B 3/10

[58] Field of Search .......... 161/109, 110, 111, 112, 161/113, 130; 128/82, 156, 284, 296; 5/91, 354, 345 R; 428/131, 132, 136, 138, 155, 179, 183, 188

[56] References Cited

UNITED STATES PATENTS

| | | | |
|---|---|---|---|
| 2,027,810 | 1/1936 | Cooper | 428/132 |
| 2,570,011 | 10/1951 | Stemberger | 128/287 |
| 3,156,242 | 11/1964 | Crowe, Jr. | 128/296 |
| 3,231,454 | 1/1966 | Williams | 161/113 |
| 3,292,619 | 12/1966 | Egler | 128/156 |
| 3,426,754 | 2/1969 | Bierenbaum et al. | 128/156 |
| 3,446,208 | 5/1969 | Fukuder | 161/112 |
| 3,546,327 | 12/1970 | Rude | 161/110 |
| 3,628,720 | 12/1971 | Schnedding | 161/112 |

*Primary Examiner*—Harold Ansher
*Attorney, Agent, or Firm*—Elliot A. Lackenbach; John V. Gorman; Richard C. Witte

[57] ABSTRACT

Absorptive device having a breatheable backsheet resistant to aqueous liquid passage, wherein the backsheet has bosses and small apertures at the apex of the bosses, the apexes of the bosses being located adjacent the absorbent body with which the backsheet is associated.

17 Claims, 4 Drawing Figures

ABSORPTIVE DEVICES HAVING POROUS BACKSHEET

FIELD OF THE INVENTION

This invention relates generally to a breatheable backsheet for absorbent devices, including disposable diapers, sanitary napkins, disposable bed pads, and incontinent pads.

DESCRIPTION OF THE PRIOR ART

Absorptive devices, such as diapers, are well-known. These devices are used to absorb liquid from the human body and retain that liquid. It is also known to cover the exterior of these devices with a flexible, plastic sheet to prevent the liquid absorbed from striking through the absorptive device and soiling other wearing apparel. The waterproof, plastic sheet of the prior art does prevent strikethrough and helps contain the liquid within the device, but it also makes the absorptive device feel hot and uncomfortable to wear and can create a rash or irritation. In addition, it precludes a self-drying of the absorptive device by evaporation of the fluid held therein. The breatheable backsheet as herein described is of particular advantage when used in absorptive devices which are worn for extended time periods when it is desirable to shield the liquid in the absorbent body thereof from adjacent clothing. Such absorptive devices include diapers, catamenial napkins, and surgical dressings.

Suggestions for permeable backsheets have been made in the art with the purpose of allowing some circulation of air between the interior of the absorptive device and the surrounding atmosphere. U.S. Pat. No. 2,570,011, issued to Stamberger on Oct. 2, 1951, approaches the problem of providing a breatheable backsheet for absorptive devices by teaching a diaper having both absorbent and retarding sections. The retarding section is a chemically treated portion of a cloth diaper and is folded toward the outside thereof. This retarding section is treated to prevent penetration of urine. U.S. Pat. No. 3,156,242, issued to Crowe, Jr., on Nov. 10, 1964, teaches an absorbent device having an absorbent body covered by a non-absorbent, flexible film. The film is air pervious so as to permit drying of the absorbent body held thereunder. The air perviousness of the film is achieved by using a microporous film or a film having holes or slits therein. U.S. Pat. No. 2,027,810, issued to Cooper on Jan. 14, 1936, teaches a film having apertured bosses therein which is designed to be liquid pervious. Additional prior art relating to porous thermoplastic webs associated with an absorbent body is U.S. Pat. No. 3,292,619, issued to Egler on Dec. 20, 1966; U.S. Pat. No. 3,426,754, issued to Bierenbaum et al on Feb. 11, 1969; and U.S. Pat. No. 3,446,208, issued to Fukuda on May 27, 1969.

The prior art does not provide a porous backsheet which is liquid impervious when the absorbent body with which it is associated is subjected to the typical pressures imposed thereon during wearing. Another problem not resolved in the prior art is that of providing a perforated backsheet which substantially retains its strength after it is perforated.

OBJECTS OF THE INVENTION

It is one object of the present invention to provide a backsheet for an absorbent body which is gas pervious and liquid impervious.

It is another object of this invention to provide a backsheet for an absorbent body which remains liquid impervious even when the absorbent pad is subjected to pressure.

It is a further object of this invention to provide a backsheet for an absorbent body which is perforated and substantially retains its strength.

It is an additional object of this invention to provide a backsheet for an absorbent body which is porous and wherein the pores tend to close when subjected to pressure.

SUMMARY OF THE INVENTION

In accordance with the present invention, there is provided an absorptive device having an absorbent body and a substantially liquid impervious backsheet underlying the absorbent body. The backsheet has a plurality of bosses therein and substantially each boss has an aperture such that each aperture forms a pore in the backsheet. When the absorptive device is placed to receive liquids from a human body such that the absorptive body is positioned between the human body and the backsheet, the liquids absorbed by the absorbent body are contained within the absorptive device and water vapor formed within the absorptive device by human body heat escapes through the pores in the backsheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which, taken in connection with the accompanying drawings, in which the thicknesses of some of the material are exaggerated for clarity and in which:

DETAILED DESCRIPTION OF THE INVENTION

Figure 1:
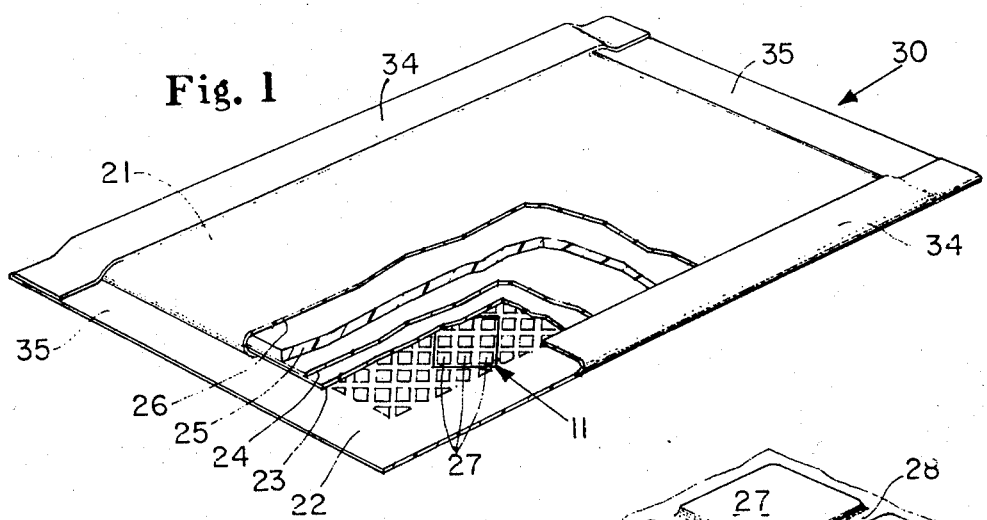
FIG. 1 is a perspective of a diaper of this invention in an unfolded condition and having various layers cut away.

Referring now to the drawings and particularly to FIG. 1 thereof, an absorptive device of this invention is illustrated, in particular, a disposable diaper 30 is illustrated. The diaper 30 is fabricated from the usual multiple layers of various materials which may typically include tissue paper, crepe paper, nonwoven fabrics, suitable absorptive fillers —such as wadding, cellulose fluff, airfelt materials, absorptive natural sponges or other foamed absorptive materials —and liquid impervious sheets in suitable combinations as will be appreciated by those familiar with the art.

The preferred construction of the diaper illustrated in FIG. 1 comprises a backsheet 22 which is generally a flexible, liquid impervious web of a thermoplastic material, this being the sheet which is normally furthest removed from the skin of the infant and prevents liquid absorbed within the absorbent body 21 from striking through and wetting adjacent clothing. The absorbent body 21 is superposed over the backsheet 22 and generally is made up from bottom tissues 23 and 24, absorbent core 25, and topsheet 26 as are well-known to those familiar in the art and more specifically described in U.S. patent Re-issue 26,151, issued to Duncan et al on Jan. 31, 1967, said re-issue patent being incorporated herein by reference. Also, the absorbent body and the backsheet are generally attached adjacent their edges and/or ends, thereby leaving their central portion free of attachment. Of course, it is also well-known to attach them along substantially their entire interface.

The backsheet 22, as mentioned above, is generally a flexible web of a thermoplastic material. In a preferred embodiment, the backsheet 22 is a 1¼ mil thick web of polyethylene film made from Alathon 3120 resin available from E. I. Du Pont de Nemours & Co. Of course, other materials will work for the backsheet 22, the primary requirements being that the backsheet 22 is flexible, fluid impervious, elastic and embossable.

Figure 2:
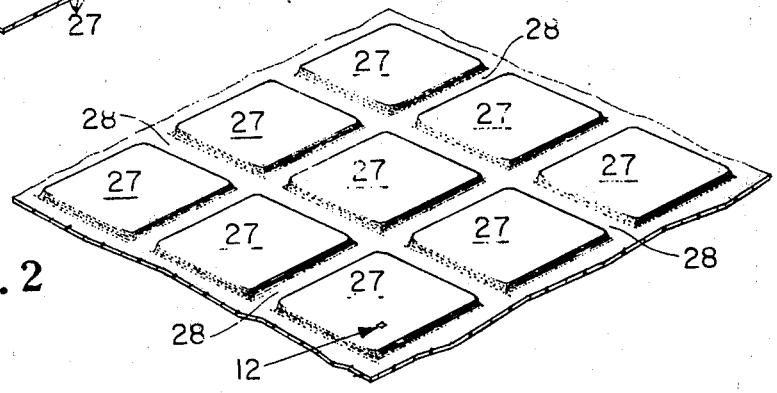
FIG. 2 is a perspective enlargement of the portion of the backsheet denoted by 11 in FIG. 1.

The backsheet 22 is embossed and perforated as shown in the drawings and has both embossed areas 27 and unembossed areas 28 interspersed between the embossed areas 27 as shown in FIG. 1 and in more detail in FIG. 2. The unembossed areas 28 lie between the embossed areas 27 to provide areas resistant to tearing between the embossed areas 27. The tear resistant unembossed areas 28 are provided to halt the progression of any tear that should originate in an embossed area 27 during wearing of an absorbent device of this invention, such as a disposable diaper.

Figure 3:
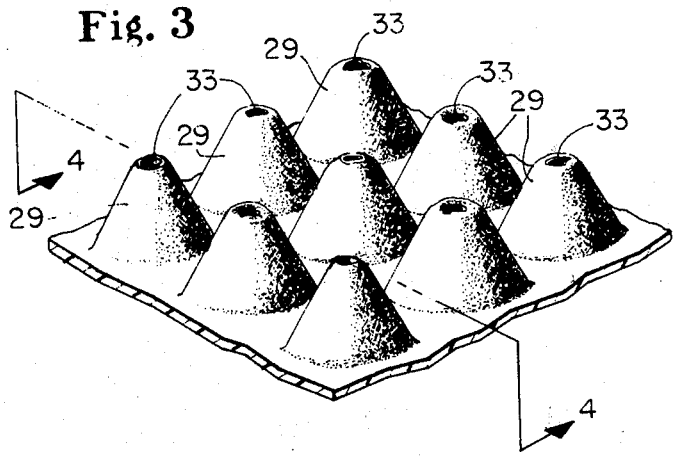
FIG. 3 is a perspective enlargement of an area of the backsheet denoted by 12 in FIG. 2.
Figure 4:
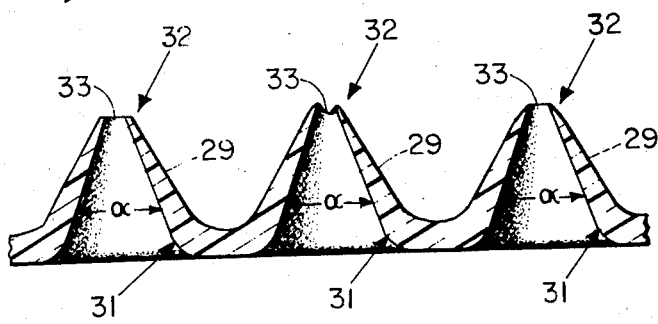
FIG. 4 is a cross-section taken along line 4—4 of FIG. 3.

In a preferred embodiment of the backsheet 22 the bosses 29 are grouped in patterns and each pattern forms an embossed area 27. These bosses 29 in a preferred embodiment are conical as shown in FIGS. 3 and 4 and have an included angle, denoted by $\alpha$ in FIG. 4, of between about 30° and 135°, preferably being between about 60° and 100°. Such an angle provides thickness to the backsheet 22 and also provides a boss 29 which will collapse, i.e., the opposite walls of the boss 29 will come together, when pressure is exerted on the diaper in use. It is thought that collapsing of the bosses 29 under pressure is advantageous because collapsing tends to close the aperture and prevent fluid from penetrating the backsheet when pressure is applied thereto, for example, when a baby sits on a wetted portion of a diaper.

Also a preferred construction of these bosses is one wherein the wall thickness of the boss 29 is thicker at the base 31 of the boss 29 than the wall thickness of the boss at the apex 32 of the boss 29 as is clearly illustrated in FIG. 4. This thinness at the apex 32 is considered desirable because it is hypothesized that the apex 32 of the boss 29 then will be more deformable under pressure and thus collapse and close the aperture when pressure is applied.

Although conical bosses are shown and mentioned as a preferred embodiment for this invention, other geometrically shaped bosses can also be used, one of which would be a pyramidal shaped boss. Regardless of the shape of the boss, the included angle within the boss is the angle existing between opposite interior walls of the boss.

In a preferred embodiment of this backsheet, the bosses 29 are substantially equal in height and regularly spaced. It has been found that a backsheet having bosses 75 to 100 micrometers in height (a micrometer being meters $\times 10^{-6}$) and a center-to-center distance between bosses of approximately 230 micrometers has performed well. It is also preferred that the boss height (hereinafter defined) is at least 1½ times the backsheet web thickness and more preferably at least 2 times the backsheet web thickness.

The bosses 29 have apertures 33 therewithin to form pores in the backsheet through which heat and vapors can escape but which substantially prevent the movement of liquid therethrough, even if the liquid is under a slight pressure. It is preferable that an aperture 33 within the boss 29 is at or near the apex 32 of that boss. The apertures 33 should have a maximum diameter of about 100 micrometers, preferably a maximum of about 50 micrometers, and most preferably a maximum of about 10 micrometers, to offer resistance to the passage of liquid through the apertures when a liquid laden absorbent body is subjected to pressure. Diameter as used herein is intended to mean an approximate average of the chords passing through the center of the aperture. The diameter of the apertures in the backsheet as used in this invention must be a compromise between a size which will provide enough open area to permit vapor to escape from the absorptive device of this invention during use and a size which will prevent the passage of fluid through these apertures. The apertures 33 preferably should have a diameter which is substantially larger than the thickness of the film in the area of the boss surrounding the aperture.

Also, the apertures 33 should have a periphery which is substantially smooth as is shown in FIG. 3. That is, the edge of the apertures are free from stress concentration points such as cracks or fissures. Apertures which include stress concentrations in a thin thermoplastic film severely weaken the film and promote rips therein during ordinary use, such as during wearing of a disposable diaper.

The apertures 33 provide the open area of the backsheet 22 through which heat and vapor can pass. This open area is determinative of the amount of vapor which can escape from the backsheet within a given time period. To be effective in releasing vapor and heat from the interior of an absorptive device of this invention, the apertures 33 should be substantially uniformly distributed over the area of the backsheet through which transmission is desired and the open area of the backsheet should be in the range of about ½% to about 10% of the available area of the backsheet and preferably in the range of from about 1% to about 5% of the available area of the backsheet. The available area of the backsheet as used herein is intended to mean that theoretical area through which permeation could occur if the entire backsheet was permeable. Such an available area would exclude at least the folded over edges 34 and the ends 35 of the backsheet as pointed out in FIG. 1. Edges 34 and ends 35 are not part of the available area of the backsheet because they do not form part of the barrier between the absorbent body 21 and the atmosphere surrounding the absorptive device when the absorptive device is in use.

The strength of the backsheet as disclosed herein particularly a thermoplastic web, is dependent on many factors, several of which are web thickness, resin formulation, and ratio of embossed area to unembossed area. In the backsheet as particularly described herein, it has been found that the ratio of the area of the bossed areas 27 to the area of the unbossed areas 28 is important for providing a backsheet 22 wherein the propagation of any tear which develops therein is inhibited. An embodiment wherein the ratio of the bossed area to the unbossed area is no greater than about 3:1 is considered to be acceptable. In addition, it is preferable that each pattern of bosses 29 forming a bossed area 27 is less than about 1 square inch and that each bossed area 27 be separated from its adjacent bossed area 27 by at least ⅛ inch of unbossed backsheet.

The backsheet 22 has been found to be more liquid impervious with the bosses 29 pointed toward the absorbent body 21; therefore, it is preferable that the bosses 29 are pointed toward the absorbent body 21. In this configuration, the bosses are not necessarily protruded into the absorbent body. In fact, the primary contact between the backsheet and the absorbent body is thought to be at the apex of the bosses. This preferred structure positions the apexes 32 of the bosses 29 adjacent the absorbent body 21 as is shown in the series of FIGS. 1, 2 and 3.

Sample absorptive devices of the subject invention were made in accordance with the following: A sheet of 1.25 mil polyethylene film made from Alathon 3120 resin was embossed and perforated such that individual bosses were made in regular patterns. Each pattern was ½ inch by ½ inch square, thus forming embossed areas ½ by ½ inch square. Each pattern was separated from its adjacent patterns by ⅛ inch wide areas which were not embossed. The bosses within each pattern were substantially conical and had an aperture at the apex thereof. The included angle within each boss was approximately 75° to 80° and the boss height from the back side of the polyethylene film, i.e., that side furthest from the apex of the boss, was about 75 micrometers. The diameter of the aperture in each boss was approximately 50 micrometers and the center-to-center distance between adjacent bosses was approximately 230 micrometers. Therefore, this embossed apertured thermoplastic sheet had an open area which was about 2.0 percent of the available area of the thermoplastic sheet.

A 4 by 4 inch square absorbent body was superposed and centrally located on a 4½ inch by 4½ inch square of the embossed apertured backsheet. The edges of the square embossed patterns in the backsheet were diagonal to the edges of the absorbent body such as is illustrated in FIG. 1 of the drawings. The absorbent body comprised a substantially uniform layer of airfelt having a basis weight of approximately 0.017 grams per square centimeter (g/sq. cm.) and tissue layers having a total basis weight of approximately 0.004 g/sq. cm. so that the total basis weight of the absorbent body was approximately 0.021 g/sq. gm. The edges of the backsheet were folded around and on top of the edges of the absorbent body and fixed thereto with adhesive.

EXAMPLE I

One of the previously described samples was "loaded" with 6 grams of liquid per gram of absorbent body of the sample. The liquid was a 1% aqueous NaCl solution reduced in surface tension to 45 dynes per centimeter with Triton X-100 surfactant available from Rohm & Haas Chemical Co. The bosses in the backsheet of this sample were pointed toward the absorbent body of the sample. The liquid loaded sample was placed with the embossed apertured backsheet downward and in contact with two plies of 12 centimeter diameter Whatman No. 4 filter paper (available from W. and R. Balston Limited, England). That is, the backsheet was intermediate the absorbent body and the filter paper. The liquid loaded sample was then pressurized, i.e., subjected to a pressure of 70.4 grams per square centimeter over a circular area of 19.7 square centimeters which is about 1.0 psi. The filter paper was weighed prior to placing the liquid loaded pressurized sample in contact therewith. The liquid imperviousness of the backsheet in the sample was measured as follows: The liquid loaded, pressurized sample was in contact with the filter paper for 2 minutes; the filter paper was removed and reweighed; the filter paper was similarly placed in contact with the liquid loaded, pressurized sample for an additional 5 minutes; the filter paper was removed and reweighed; the filter paper was similarly placed in contact with the liquid loaded, pressurized sample for an additional 8 minutes; and the filter paper was removed and reweighed. The amount of liquid absorbed by the filter paper in 2 minutes, 7 minutes and 15 minutes was 0.08, 0.13 and 0.16 grams, respectively, as noted in Table I below.

The embossed apertured backsheet having the bosses pointed toward the absorbent body provided a substantially fluid impervious barrier to the liquid under pressure in the absorbent body.

Example II was performed with a sample identical to that used in Example I except that the conical bosses were pointed outwardly, i.e., away from, rather than inwardly toward the absorbent body. The liquid loading and pressurizing of the sample and the liquid imperviousness test procedure used in Example II was the same as that for Example I. The results of the liquid imperviousness test for Example II are given below in Table I.

The embossed apertured backsheet having the bosses pointed away from the absorbent body provided a satisfactory barrier to the liquid within the absorbent body, although the barrier provided was somewhat less than that displayed in Example I.

EXAMPLE III

The sample used herein was the same as that used in Example I. The sample was loaded with 6 grams of the 45 dyne per centimeter liquid per gram of absorbent body in the pad and the liquid was then sealed in the sample by placing an unperforated sheet of the polyethylene film over the surface of the sample opposite that surface covered by the embossed apertured backsheet. The unperforated sheet was attached to the sample with plastic tape to form an encased absorbent body. This sample with an encased absorbent body was then placed with the embossed, apertured backsheet facing upward on a table for approximately 16 hours and the ambient room condition (approximately 70°F.) evaporative loss was determined by subtracting the weight of the fluid loaded sample after 16 hours from the initial weight of the fluid loaded sample. The effective area of the embossed apertured backsheet was reduced to approximately 3.5 inches by 3.5 inches due to covering of part of the edge by the plastic tape used to secure the unperforated polyethylene sheet to the sample. The evaporative loss of fluids from the sample was 9.0 grams which was 0.71 grams per hour per 100 square centimeters of backsheet.

The embossed apertured backsheet having the bosses pointed toward the absorbent body provided an acceptable vapor permeable backsheet for an absorptive device.

EXAMPLE IV

The absorptive device used in Example IV was the same as that used in Example III, i.e., the liquid loaded absorbent body was encased, except that the bosses were pointed outwardly away from the absorbent body.

The evaporative loss from the sample was 9.2 grams which was 0.73 grams per hour per 100 square centimeters of backsheet.

The embossed apertured backsheet having the bosses pointed away from the absorbent body provided an acceptable vapor permeable backsheet for an absorptive device.

TABLE I

| EXAMPLE | BOSS ORIEN-TATION | TIME | LIQUID ABSORBED (G.)* AMT (G.) | EVAPORATIVE LOSS** RATE (G./ HR./ 100 CM²) |
|---|---|---|---|---|
| I | Inward | 2 min. | 0.08 | |
|  | " | 7 min. | 0.13 | |
|  | " | 15 min. | 0.16 | |
| II | Outward | 2 min. | 1.9 | |
|  | " | 7 min. | 2.2 | |
|  | " | 15 min. | 2.3 | |
| III | Inward | 16 hrs. | 9.0 | 0.71 |
| IV | Outward | 16 hrs. | 9.2 | 0.73 |

*Liquid absorbed by the filter paper through the backsheet.
**Evaporative loss through the backsheet The data of Table I show that a disposable diaper made in accordance with the teachings above would be self drying to a large extent during a night time wearing and also would provide a diaper with a backsheet which is substantially liquid impervious. A common disposable diaper has an absorbent body with lineaments of about 12 by 16 inches and contains 47 grams of absorptive material. The available area of the backsheet in such a diaper would be approximately 192 sq. in. (12×16). Thus, based on the results of Example IV, during a 12 hour wearing of such a diaper, about 107 grams of vaporized fluid could be transferred through the embossed apertured backsheet at about 70°F. In actuality, the wearer's body temperature being about 100°F. increases the amount of liquid vaporized within a diaper and driven through such a backsheet. A vapor loss mechanism of such magnitude helps prevent babies from being "soaking wet" in the morning and reduce the incidence of rash.

Thus it is apparent that there has been provided, in accordance with the invention, an absorptive device that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An absorptive device, comprising:
an absorbent body; and
a backsheet of a material having the characteristics of polyethylene film in direct contact with and substantially entirely underlying the absorbent body;
the backsheet having a plurality of tapered hollow bosses therein extending towards the absorbent body with each boss having an aperture extending through the apex thereof forming a tapered pore in the backsheet which enlarges in a direction away from the absorbent body;
the dimension of the pores being selected so that, when the absorptive device is placed to receive liquids such as discharges from a human body with the absorbent body positioned between the human body and the backsheet, the liquids absorbed by the absorbent body and contained within the absorptive device are blocked from passage through the backsheet while vapors pass readily through the pores of the backsheet.

2. The device of claim 1 wherein the bosses are essentially conical.

3. The device of claim 1 wherein the diameter of the apertures is a maximum of about 100 micrometers.

4. The device of claim 1 wherein the diameter of the apertures is a maximum of about 50 micrometers.

5. The device of claim 1 wherein the diameter of the apertures is a maximum of about 10 micrometers.

6. The device of claim 1 wherein the open area of the backsheet is in the range of from about ½ percent to about ten percent of the available area of the backsheet.

7. The device of claim 1 wherein the open area of the backsheet is in the range of from about one percent to about 5 percent of the available area of the backsheet.

8. The device of claim 1 wherein the included angle within the boss is between about 30° and 135°.

9. The device of claim 1 wherein the included angle within the boss is between about 60° and 100°.

10. The device of claim 1 wherein the wall thickness at the apex of the boss is thinner than the wall thickness at the base of the boss.

11. The device of claim 1 wherein the periphery of each aperture is substantially smooth.

12. The device of claim 1 wherein the backsheet has bossed areas and unbossed areas, the bosses being grouped in patterns to form the bossed areas and each pattern being separated from its adjacent pattern by an unbossed area, said unbossed areas extending along linear regions in a generally bilateral pattern substantially entirely of the backsheet to maintain high strength and tear resistance thereof.

13. The device of claim 12 wherein the ratio of bossed area to the unbossed area is no greater than about 3:1.

14. The device of claim 12 wherein each pattern is less than about one square inch and is separated from its adjacent patterns by at least ⅛ inch width of unbossed backsheet.

15. An absorptive device, comprising:
an absorbent body; and
a backsheet having the characteristics of polyethylene film in direct underlying contact with the absorbent body;
the backsheet having a plurality of generally conical bosses therein, each boss being provided with an aperture extending through the apex thereof;
the bosses being pointed toward the absorbent body with the apices of the bosses adjacent the absorbent body;
the included angle within each boss being between about 60° and 100°;
each aperture having a diameter which is a maximum of about 50 micrometers;
the open area of the backsheet being in the range of from about 1 to 5 percent of the available area of the backsheet;
to provide an absorptive device which retains liquids gathered therein while permitting vapor within the absorptive device to escape to the surrounding atmosphere.

16. An absorptive device defined in claim 15 wherein said backsheet comprises polyethylene film.

17. An absorptive device defined in claim 16 wherein said absorbent body comprises a generally flat bilaterally extensive pad and said backsheet extends substantially entirely across at least an outer face thereof.

* * * * *